(12) United States Patent
Lu (10) Patent No.: US 11,529,118 B2
(45) Date of Patent: Dec. 20, 2022

(54) ULTRASOUND SYSTEM AND METHOD FOR DETECTION OF KIDNEY STONES USING TWINKLING ARTIFACT

(71) Applicant: KONINKLIJKE PHILIPS N.V., Eindhoven (NL)

(72) Inventor: Wei Lu, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 174 days.

(21) Appl. No.: 16/461,016

(22) PCT Filed: Nov. 9, 2017

(86) PCT No.: PCT/EP2017/078694
§ 371 (c)(1),
(2) Date: May 15, 2019

(87) PCT Pub. No.: WO2018/091341
PCT Pub. Date: May 24, 2018

(65) Prior Publication Data
US 2019/0298300 A1    Oct. 3, 2019

Related U.S. Application Data

(60) Provisional application No. 62/423,424, filed on Nov. 17, 2016.

(51) Int. Cl.
*A61B 8/08* (2006.01)
*A61B 8/14* (2006.01)
(Continued)

(52) U.S. Cl.
CPC ............... *A61B 8/085* (2013.01); *A61B 8/14* (2013.01); *A61B 8/145* (2013.01); *A61B 8/463* (2013.01);
(Continued)

(58) Field of Classification Search
CPC ......... A61B 8/54; A61B 8/488; A61B 8/5269; A61B 8/085; A61B 8/145; A61B 8/5246; A61B 8/467
See application file for complete search history.

(56) References Cited

U.S. PATENT DOCUMENTS 5,706,818 A * 1/1998 Gondo ................ G01S 15/8979
600/447
5,833,614 A * 11/1998 Dodd .................... G01S 15/107
600/447
(Continued)

FOREIGN PATENT DOCUMENTS

JP    2001269344 A  * 10/2001  ............... A61B 8/06
JP    2002301077 A  * 10/2002

OTHER PUBLICATIONS

JP-2001269344-A (Year: 2001).*
(Continued)

*Primary Examiner* — Joel Lamprecht
*Assistant Examiner* — Nyrobi Celestine (57) ABSTRACT

A method color Doppler imaging in accordance with some examples of the present disclosure includes transmitting with a probe of an ultrasound imaging system, ultrasound pulses towards a region of interest in a subject, receiving with the probe echoes responsive to the pulses, generating B-mode image data and Doppler signals based on the ultrasound echoes, filtering the Doppler signals, wherein the filtering includes rejecting lower intensity signals which have amplitudes below a threshold amplitude and passing higher intensity signals which have amplitudes above the threshold amplitude, generating color data based on the higher intensity signals, overlaying the color data with the B-mode image data to produce a color Doppler image, and displaying the color Doppler image in a kidney stone detection interface.

17 Claims, 6 Drawing Sheets

(51) Int. Cl.
A61B 8/00 (2006.01)
G01S 15/89 (2006.01)
G01S 7/52 (2006.01)

(52) U.S. Cl.
CPC ............ *A61B 8/488* (2013.01); *A61B 8/5207* (2013.01); *A61B 8/5223* (2013.01); *A61B 8/5246* (2013.01); *A61B 8/5269* (2013.01); *A61B 8/54* (2013.01); *G01S 7/52036* (2013.01); *G01S 15/8979* (2013.01); *A61B 8/4438* (2013.01); *A61B 8/467* (2013.01); *A61B 8/483* (2013.01); *G01S 15/895* (2013.01)

(56) References Cited

U.S. PATENT DOCUMENTS

| | | | | |
|---|---|---|---|---|
| 5,855,556 | A * | 1/1999 | Shirai | G01S 15/8979 600/455 |
| 5,967,985 | A * | 10/1999 | Hayakawa | A61B 8/0833 600/440 |
| 6,050,944 | A | 4/2000 | Holley et al. | |
| 6,123,672 | A * | 9/2000 | Miller | G01S 7/52025 600/455 |
| 7,846,098 | B2 * | 12/2010 | Bakircioglu | A61B 8/06 600/440 |
| 7,901,358 | B2 * | 3/2011 | Mehi | G10K 11/346 600/447 |
| 8,157,734 | B2 * | 4/2012 | Nakata | G01S 7/52085 600/440 |
| 8,858,446 | B2 * | 10/2014 | Sato | A61B 8/06 600/454 |
| 2003/0045795 | A1 * | 3/2003 | Bjaerum | G01S 15/8979 600/441 |
| 2005/0059892 | A1 * | 3/2005 | Dubois | A61B 8/461 600/443 |
| 2005/0251041 | A1 | 11/2005 | Moehring | |
| 2007/0239001 | A1 | 10/2007 | Mehi et al. | |
| 2008/0194950 | A1 * | 8/2008 | Mejia | A61B 8/467 600/437 |
| 2009/0281426 | A1 * | 11/2009 | Miyaki | A61B 8/463 600/443 |
| 2011/0152689 | A1 * | 6/2011 | Sato | A61B 8/06 600/454 |
| 2011/0263967 | A1 | 10/2011 | Bailey et al. | |
| 2011/0263985 | A1 * | 10/2011 | Gauthier | A61B 8/0833 600/454 |
| 2014/0194737 | A1 | 7/2014 | Bailey et al. | |
| 2015/0141821 | A1 | 5/2015 | Yoshikawa et al. | |
| 2015/0282787 | A1 * | 10/2015 | Sato | A61B 8/488 600/441 |
| 2015/0305760 | A1 | 10/2015 | Owen et al. | |
| 2015/0320383 | A1 | 11/2015 | Dunmire et al. | |
| 2015/0320384 | A1 | 11/2015 | Cunitz et al. | |
| 2016/0082291 | A1 | 3/2016 | Bailey et al. | |
| 2016/0310110 | A1 | 10/2016 | Dodd et al. | |

OTHER PUBLICATIONS

International Search Report and Written Opinion for International Application No. PCT/EP2017/078694, filed Nov. 9, 2017, 14 pages.
Cunitz, et al., "Improved Detection of Kidney Stones Using an Optimized Doppler Imaging Sequence", 2014 IEEE International Ultrasonics Symposium Proceedings, Sep. 3, 2014, pp. 425-455.
Aytac, et al., "Effect of Color Doppler System on the Twinkling Sign Associated with Urinary Tract Calculi", Journal of Clinical Ultrasound, Oct. 1, 1999, vol. 27, No. 8, Oct. 1999, pp. 433-439.
Kamaya, et al., "Twinkling Artifact on Color Doppler Sonography: Dependence on Machine Parameters and Underlying Cause", Jan. 1, 2003, pp. 215-222, Retrieved from the Internet: URL:https://www.ajronline.org/doi/pdf/10.2214/ajr.180.1.1800215.
Shabana, et al., "Comparison Between Color Doppler Twinkling Artifact and Acoustic Shadowing for Renal Calculus Detection:", Ultrasound in Medicine and Biology, vol. 35, No. 2, pp. 339-350.

* cited by examiner

ULTRASOUND SYSTEM AND METHOD FOR DETECTION OF KIDNEY STONES USING TWINKLING ARTIFACT

This application is the U.S. National Phase application under 35 U.S.C. § 371 of International Application No. PCT/EP2017/078694, filed on Nov. 9, 2017, which claims the benefit U.S. Provisional Application Ser. No. 62/423,424, filed Nov. 17, 2016. These applications are hereby incorporated by reference herein.

This application relates to ultrasonic imaging, and specifically to the use of color Doppler imaging operated in a specific mode configured for kidney stone detection.

Kidney stone disease afflicts about 10% of the U.S. population and severely affects the life quality of patients. Typically, the preferred imaging modality for detecting kidney stones is computed tomography (CT). While the use of ultrasound, and specifically the use of the twinkling artifact (TA) in color Doppler ultrasound imaging has been proposed, it has had limited success in detecting kidney stones. The twinkling artifact (TA) appears on a kidney stone as a dynamic changing ultrasound color display. Studies indicate that a major contributor to the TA is the microbubbles which may be found on the surface of the kidney stone. Although TA has been used in past to assist in kidney stone detection, the diagnosis accuracy of using TA for kidney stone detection is highly dependent sonographer skills, physician's experiences, and certain ultrasound system setting or parameters. The instability of the TA has prevented it from being adopted clinically as a reliable tool for kidney stone detection.

Existing ultrasound machines are frequently equipped with color Doppler imaging capabilities. In the color flow imaging mode (sometimes referred to simply as color Doppler or velocity mode), echoes reflected form moving tissue (e.g., blood flow) is used to determine the direction and velocity of flow. In contrast to the more widely used velocity mode, the power (angio) mode determines the frequency shift of the reflected echoes from the ultrasound energy. In the power mode display, the sum of the Doppler signal intensities reflected by moving particles is represented by levels of brightness while the magnitude of the flow velocity and in some case the direction of the flow are ignored. In the velocity mode, red and blue colors are typically used to represent on a display the flow direction. In the power/angio mode higher amplitudes of the reflected ultrasound echoes are displayed in lighter shades irrespective of the frequency and flow direction. However, in both modes, the imaging parameters are typically set for detecting moving reflectors (i.e., blood flow) and are thus are not optimal for other purposes.

SUMMARY

A method according to one embodiment may include transmitting with a probe of an ultrasound imaging system, ultrasound pulses towards a region of interest in a subject, receiving with the probe echoes responsive to the pulses, generating B-mode image data and Doppler signals based on the ultrasound echoes, filtering the Doppler signals, wherein the filtering includes rejecting lower intensity signals which have amplitudes below a threshold amplitude and passing higher intensity signals which have amplitudes above the threshold amplitude, generating color data based on the higher intensity signals, overlaying the color data with the B-mode image data to produce a color Doppler image, and displaying the color Doppler image in a kidney stone detection interface.

In some examples, the filtering of the Doppler signals is performed responsive to a selection of one of a plurality of color Doppler imaging modes, the method further comprising filtering the Doppler signals to reject signals above the threshold amplitude responsive to a selection of another one of the plurality of color Doppler imaging modes. In some examples, the method may further include providing a user interface for adjusting the threshold amplitude, the transmit frequency, a pulse duration, a pulse repetition frequency, of combinations thereof.

In some example, the method may include transmitting first ultrasound pulses having a first pulse duration when imaging in a first color Doppler imaging mode and transmitting second ultrasound pulses having a second pulse duration shorter that the first pulse duration when imaging in a second color Doppler imaging mode. In some examples, the first ultrasound pulses comprise pulses having 6 or greater number of cycles per pulse and wherein the second ultrasound pulses comprise pulses having 5 or fewer number of cycles per pulse.

In some examples, the method may include activating, responsive to user input, one or a plurality of color Doppler imaging modes of the ultrasound imaging system and automatically setting, responsive to said activating, the transmit frequency to the center frequency of the probe or to a frequency within 30% of the center frequency of the probe. In some examples, the method may further include automatically identifying the center frequency of the probe responsive to said activating, for example from a look up table or probe specification data stored in a memory of the ultrasound system.

Any of the methods described herein for ultrasonically detecting kidney stones may be embodied in executable instructions stored on non-transitory computer-readable medium, which when executed by one or more processor of an ultrasound system, cause the one or more processors to perform the method embodied thereon.

In some examples, an ultrasound system according to the present disclosure may include a user interface configured to receive user input for selecting one of a plurality of color Doppler imaging modes, and a non-transitory memory which stores a plurality of pulse configuration parameters including a first set of pulse configuration parameters associated with a first color Doppler imaging mode and a second set of pulse configuration parameters associated with a second color Doppler imaging mode. The system may further include a probe configured to transmit ultrasound pulses to a region of interest in a subject and receive ultrasound echoes responsive to the pulses and a transmit controller configured to cause the probe to transmit first pulses in accordance with the first set of pulse configuration parameters responsive to a selection of the first color Doppler imaging mode and second pulses in accordance with the second set of pulse configuration parameters responsive to a selection of the second color Doppler imaging mode, wherein the first pulses are longer than the second pulses. The system may further include a signal processor configured to generate echo signals based on ultrasound echoes received by the probe, a B-mode processor configured to generate B-mode image data based on the echo signals, and a Doppler processor configured to generate Doppler signals based on the echo signals. The Doppler processor may be further configured, responsive to the selection of the second color Doppler imaging mode, to filter out the Doppler signals below a threshold amplitude, retain the Doppler signals above the threshold amplitude, and generate color data for only the retained Doppler signals. The system may include a display configured to display an overlay of the B-mode image data and the color data.

In some embodiments, the Doppler processor may be further configured to filter out Doppler signals above the threshold amplitude responsive to the selection of the first color Doppler imaging mode. In some embodiments, the Doppler processor may include an amplitude threshold filter configured to filter out the Doppler signals below the threshold amplitude and a wall filter configured to filter out signals below a predetermined frequency. In some embodiments, the threshold amplitude may be selected to correspond to an echo intensity of at least 40 dB above an echo intensity associated with a fluid or soft tissue.

In some embodiments, the non-transitory memory of the system may further store executable instructions for automatically identifying, responsive to the selection of the second color Doppler imaging mode, the center frequency of the probe coupled to the system and setting the transmit frequency for the second pulses to the center frequency of the probe or to a frequency within 30% of the center frequency of the probe. In some embodiments, the user interface may be further configured to receive user input for adjusting the transmit frequency, the pulse duration, the PRF, and combinations thereof. In some examples, the pulse duration may be set to 4 or fewer cycles per pulse.

DESCRIPTION

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

In accordance with principles of the present invention, an ultrasound system may include a Doppler processor which may be configured to generate color data from Doppler signals for providing conventional colorflow and color power angio (CPA) images and which is additionally or alternatively configured to generate color information from the Doppler signals for the purposes of detecting kidney stones. While examples are described herein with reference to kidney stones, it will be appreciated that the systems and methods of the present disclosure may be equally applicable to the ultrasonic detection of other types of stones or calculi as may be found in an organ, duct or vessel of a subject.

Color Doppler is an ultrasonic imaging mode which has become widespread for use in imaging moving tissue. For example, Colorflow Doppler is frequently used to analyze blood flow (e.g., determine velocity and direction of the flow). More recently, ultrasonic Doppler techniques have been extended to detection, display and measurement of tissue motion, such as to study the moving heart and vascular walls. Analysis of tissue motion is performed by means of spectral Doppler as wells as Colorflow Doppler imaging techniques. Color Power Angio (CPA), sometimes simply referred to as Power Doppler, is another color Doppler method for providing color data reflective of the Doppler signals. Unlike Colorflow Doppler, Power Doppler depicts the amplitude, or power, of the Doppler signals rather than the velocity—directional and velocity information is not available via the Power Doppler method. Typically, Doppler imaging techniques, which are used to image blood flow and moving tissue, utilize signals above certain Doppler shift frequencies and below certain amplitudes, and signals which are below the relevant Doppler shift frequencies and above the relevant amplitudes are considered to constitute noise or clutter. Thus, the signals which are below the relevant Doppler shift frequencies and above the relevant amplitudes are typically filtered out (e.g., by a wall filter or another type of filter) before the color data is displayed.

In contrast, examples in accordance with the present disclosure reverse this typical process in that signals below a threshold amplitude are discarded as they likely correspond to moving tissue, while signals above the threshold amplitude are retained and utilized for generating the color data. The signals with higher amplitudes that constitute noise or clutter in blood flow analysis are likely based on ultrasound reflecting from highly echogenic and likely stationary objects, such as kidney stones. The echogenicity of kidney stones has been attributed to the presence of microbubbles on the surface of the stone. Thus, in accordance with the examples herein, the Doppler signals which are generally responsible for producing the Twinkling Artifact may be isolated and enhanced for use in kidney stone detection.

Typically, pulsed-wave, or simply pulsed, ultrasound is used to obtain color Doppler images. In pulsed ultrasound, a transmit pulse is a series of individual cycles that travel together as a single unit. Thus, a longer pulse can be said to include a larger number of cycles than a relatively shorter pulse. The number of cycles in a given pulse is defined by the pulse duration parameter, thus a longer pulse is said to have a longer pulse duration while a shorter pulse is said to have a shorter pulse duration. For example, for conventional Doppler imaging (Colorflow or CPA), longer pulses (e.g., on the order of 6-12 cycles) are typically used. This is generally due to the fact that the Doppler shift is being estimated at a large number of points in the image field, thus the time required to acquire the ultrasound data for one colorflow image is relatively long. This is because the Doppler technique requires each point where flow is to be determined to be sampled numerous times (ensemble length) at a chosen sampling rate (pulse repetition frequency, or PRF). In contrast, in accordance with the present disclosure, much shorter pulses can be used for generating the color data for producing the Twinkling artifact since the signals of interest are obtained from non-moving object. Thus, the overall frame rate for obtaining useful color data e.g., for kidney stone detection, can be increased. In some examples, pulses of up to 2 cycles, 3 cycles, or 4 cycles may be used to more efficiently acquire the color data for kidney stone detection. In other examples, longer pulses may be used.

Figure 1:
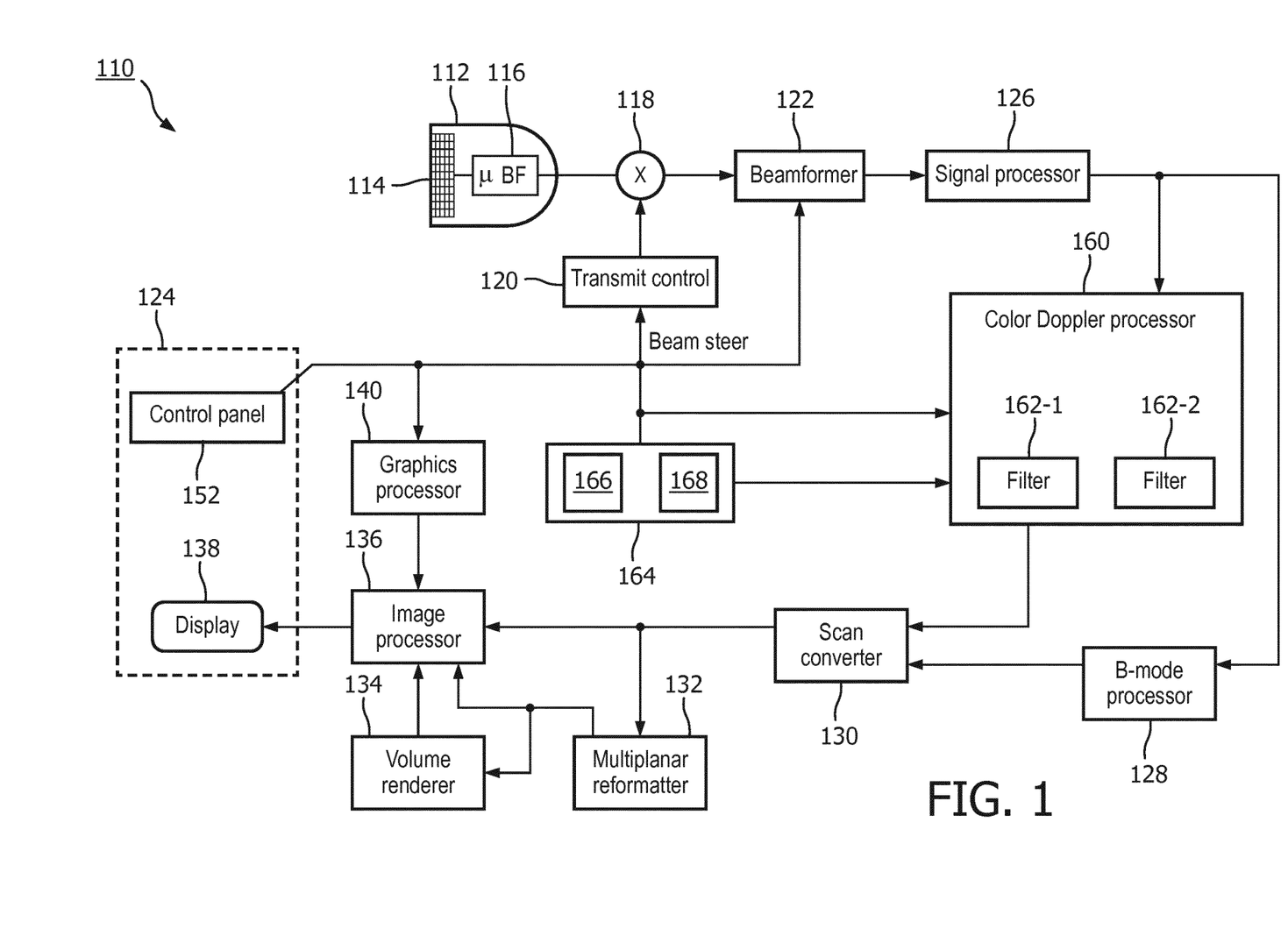
FIG. 1 is a block diagram of an ultrasound imaging system for kidney stone detection in accordance with the present disclosure.

FIG. 1 shows a block diagram of an ultrasound imaging system 100 constructed in accordance with the principles of the present disclosure. The ultrasound imaging system 100 may be configured to perform B-mode imaging, Doppler imaging, and combinations of the two.

The ultrasound imaging system 100 in the embodiment in FIG. 1 includes an ultrasound probe 112, which includes a transducer array 114 for transmitting ultrasound waves and receiving echo information. In some examples, such as for B-mode imaging and Doppler imaging, pulsed-wave ultrasound may be used. A variety of transducer arrays may be used, e.g., linear arrays, curved arrays, or phased arrays. The transducer array 114, for example, can include a two dimensional array (as shown) of transducer elements capable of scanning in both elevation and azimuth dimensions for 2D and/or 3D imaging. In some embodiments, the transducer array 114 may be coupled to a microbeamformer 116, which may be located in the ultrasound probe 112. The microbeamformer 116 controls transmission and reception of signals by the transducer elements in the array 114. In some embodiments, the functionality of the microbeamformer 116 may be provided in the system base, for example incorporating it into the function of the beamformer 122 described further below. In some embodiments, a curved array transducer, such as the Philips C5-1 probe, may be used for the probe 112.

In the illustrated example, the microbeamformer 116 is coupled by a probe cable to a transmit/receive (T/R) switch 118, which switches between transmission and reception and protects the main beamformer 122 from high energy transmit signals. In some embodiments, for example in portable ultrasound systems, the T/R switch 118 and other elements in the system can be included in the ultrasound probe 112 rather than in a separate ultrasound system base. The ultrasound system base typically includes software and hardware components including circuitry for signal processing and image data generation as well as executable instructions for providing a user interface.

The transmission of ultrasonic pulses from the transducer array 114 under control of the microbeamformer 116 is directed by the transmit controller 120 coupled to the T/R switch 118 and the beamformer 122, which may receive input from the user's operation of a user interface 124. The user interface 124 may include one or more input devices such as a control panel 152, which may include one or more mechanical controls (e.g., buttons, encoders, etc.), touch sensitive controls (e.g., a trackpad, a touchscreen, or the like), and other known input devices. The user interface 124 may be configured to display an interface for selecting a color Doppler imaging mode and the transmit controller 120 may responsively cause differently configured pulses to be transmitted by the probe. In one color Doppler imaging mode, longer pulses (e.g., 6-12 cycles per pulse or more) may be used, while in a different Doppler imaging mode, shorter pulses (e.g., 5 cycles per pulse or less, in some examples 2-4 cycles per pulse) may be used. Additionally, and responsive to the selected mode, the transmit controller 120 may cause the probe to transmit ultrasound at a frequency that is set close to the center frequency of the probe. Another function which may be controlled by the transmit controller 120 is the direction in which beams are steered. Beams may be steered straight ahead from (orthogonal to) the transducer array 114, or at different angles for a wider field of view. The partially beamformed signals produced by the microbeamformer 116 are coupled to a main beamformer 122 where partially beamformed signals from individual patches of transducer elements are combined into a fully beamformed signal. The beamformed signals are coupled to a signal processor 126.

The signal processor 126 can process the received echo signals in various ways, such as bandpass filtering, decimation, I and Q component separation, and harmonic signal separation. The signal processor 126 may also perform additional signal enhancement such as speckle reduction, signal compounding, and noise elimination. The processed signals may be coupled to a B-mode processor 128 for producing B-mode image data. The B-mode processor can employ amplitude detection for the imaging of structures in the body. The signals produced by the B-mode processor 128 may be coupled to a scan converter 130 and a multiplanar reformatter 132. The scan converter 130 is configured to arrange the echo signals in the spatial relationship from which they were received in a desired image format. For instance, the scan converter 130 may arrange the echo signal into a two dimensional (2D) sector-shaped format, or a pyramidal or otherwise shaped three dimensional (3D) format. The multiplanar reformatter 132 can convert echoes which are received from points in a common plane in a volumetric region of the body into an ultrasonic image (e.g., a B-mode image) of that plane, for example as described in U.S. Pat. No. 6,443,896 (Detmer). A volume renderer 134 may generate an image of the 3D dataset as viewed from a given reference point, e.g., as described in U.S. Pat. No. 6,530,885 (Entrekin et al.).

In parallel, the signals from the signal processor 126 may be coupled to a Doppler processor 160, which may be configured to estimate the Doppler shift and generate Doppler image data. The Doppler image data may include color data which is then overlaid with B-mode (or grayscale) image data for display. During conventional color Doppler (i.e., Colorflow or CPA) imaging when blood or moving tissue is being imaged, such as responsive to a selection of Colorflow or CPA imaging sub-modes of the system, the Doppler processor 160 may be configured to filter out unwanted signals (i.e., noise or clutter), by one or more filters 162-1, 162-2, such as by a wall filter or another type of filter, which are not associated with the blood or moving tissue of interest. In this case, the Doppler processor may pass the signals through a first filter 162-1 configured to remove lower frequency signals. The Doppler processor 160 may be further configured to estimate velocity and power in accordance with known techniques. For example, the Doppler processor may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators.

In some examples, the velocity and power estimates may undergo further threshold detection to further reduce noise, as well as segmentation and post-processing such as filling and smoothing. The velocity and power estimates are then mapped to a desired range of display colors in accordance with a color map. The color data, also referred to as Doppler image data, is then coupled the scan converter 130 where the Doppler image data is converted to the desired image format and overlaid on the B mode image of the tissue structure containing the blood flow to form a color Doppler image.

When performing color Doppler imaging in a kidney stone detection mode of the present disclosure, instead of noise or clutter filtering, the Doppler signals may undergo different type of threshold detection to retain the signals typically deemed to constitute noise and reject those signals typically retained for purposes of Colorflow or CPA imaging. As such, color data is produced or retained only for signals above a threshold amplitude (e.g., an amplitude that is 40 dB or more above the amplitude typical for blood flow or soft tissue). Similar to the colorflow and CPA modes, the color data from the kidney stone detection mode is then coupled to the scan converter 130 where it is overlaid on the B mode image of the surrounding tissue structures to form a modified Color Doppler image, as show e.g., in FIGS. 4A-4D.

Output (e.g., images) from the scan converter 130, the multiplanar reformatter 132, and/or the volume renderer 134 may be coupled to an image processor 136 for further enhancement, buffering and temporary storage before being displayed on an image display 138. A graphics processor 140 may generate graphic overlays for display with the images. These graphic overlays can contain, e.g., standard identifying information such as patient name, date and time of the image, imaging parameters, and the like. For these purposes the graphics processor may be configured to receive input from the user interface 124, such as a typed patient name or other annotations. In some embodiments, one or more functions of at least one of the graphics processor, image processor, volume renderer, and multiplanar reformatter may be combined into an integrated image processing circuitry (the operations of which may be divided among multiple processor operating in parallel) rather than the specific functions described with reference to each of these components being performed by a discrete processing unit. Furthermore, while processing of the echo signals, e.g., for purposes of generating B-mode images or Doppler images are discussed with reference to a B-mode processor and a Doppler processor, it will be understood that the functions of these processors may be integrated into a single processor.

As further shown in FIG. 1, the ultrasound system may include a memory storage device 164. The memory storage device 164 may be any suitable type of non-volatile. The memory 164 may store various configuration parameters, for example pulse configuration data 166 for setting the pulse duration of the ultrasound waves for any of the respective system modes. The memory 164 may also store executable instructions 168 for example for providing the various user interface displays associated with the different color Doppler imaging sub-modes of the system (e.g., Colorflow, CPA, kidney stone detection mode) and/or for automatically setting relevant configuration parameters responsive to the selection of a given mode. In some examples, the executable instructions 168 may include instructions for identifying the center frequency of the probe and automatically setting the transmit frequency for the scanning session to a value equal to or close to the center frequency.

Figure 2:
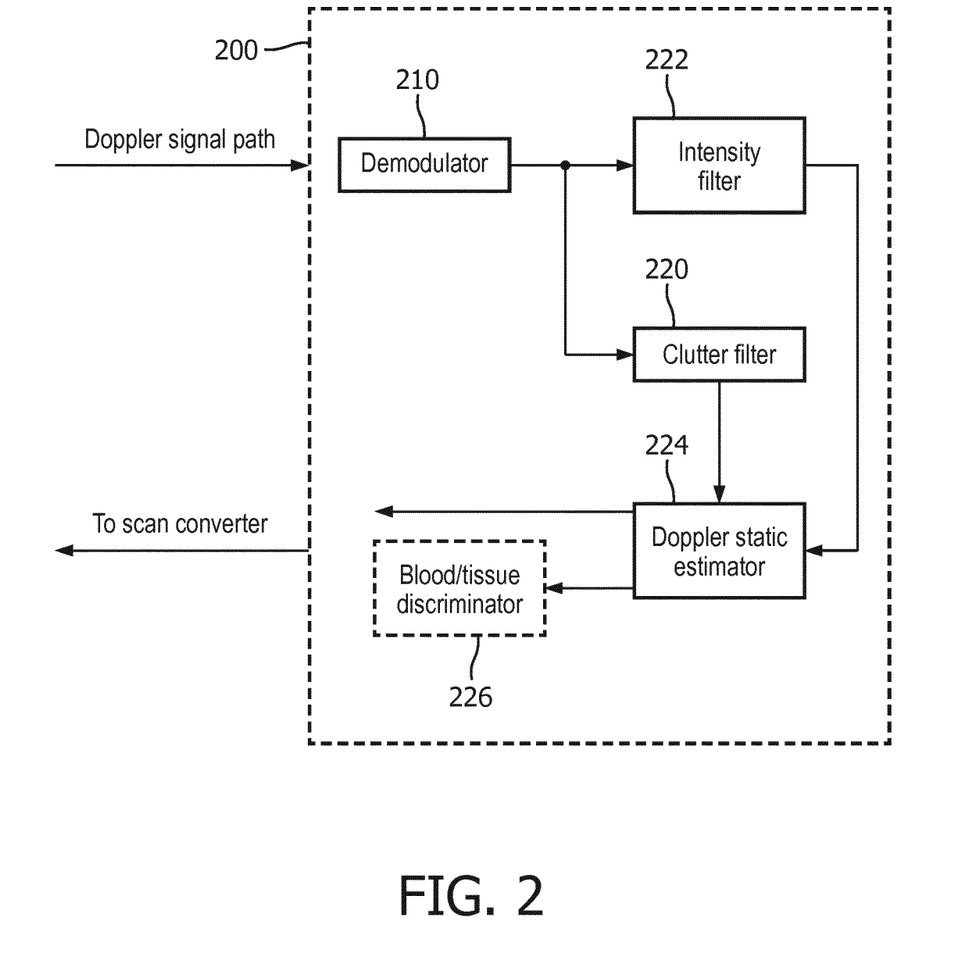
FIG. 2 is a block diagram of a Doppler processor of an ultrasound system in accordance with the present disclosure.

Referring now also to FIG. 2, further aspects of a Doppler processor in accordance with the examples herein will be described. FIG. 2 shows an example Doppler signal path and processing which may be performed by a Doppler processor in accordance with the present disclosure. Signals (e.g., I Q components of the received echoes) are coupled via the Doppler signal path to the Doppler processor 200. The Doppler processor 200 may include a demodulator 210 which extracts the Doppler frequency shift information from the ultrasound signals, as is conventionally known. The demodulated signals may then be passed through either a first filter 220 or a second filter 222, depending on the mode in which Doppler imaging is being performed. In a first Doppler imaging mode (e.g., a conventional Colorflow or CPA mode), the signals may be passed through the first filter 220, which may be a clutter filter configured to remove signals from stationary and slowly moving tissue. The clutter filter may be e.g., a wall filter configured to remove signals below a threshold frequency. The signals which are retained thus correspond to echoes received from blood flow or moving tissue, which are then utilized to generate conventional Colorflow or CPA images.

In a second Doppler imaging mode (e.g., kidney stone detection mode), the signals may be passed through a second filter 222, which may be an intensity filter configured to remove low intensity signals. For example, the intensity filter may be configured to pass signals above a given threshold amplitude and reject signals below the threshold amplitude. The threshold amplitude may be set to a value which is at least 35 dB and in some examples, at least 40 dB greater than the signal amplitude typical for blood or soft tissue, thus isolating only those signals associated with the twinkling artifact of Doppler imaging. The filtered signals may then be processed by a Doppler estimator 224 which may extract the velocity and power values (e.g., using autocorrelation or a different technique) for generating the color data for each color line in the Doppler image. In some cases, such as when performing Colorflow imaging, the signals may be further processed by an optional blood/tissue discriminator 226 to isolate for display only the color data determined to correspond to blood flow. The color data output by the Doppler processor 200 is then transmitted to the scan converter where it is combined with B-mode image data for generating the color Doppler images.

Figure 3:
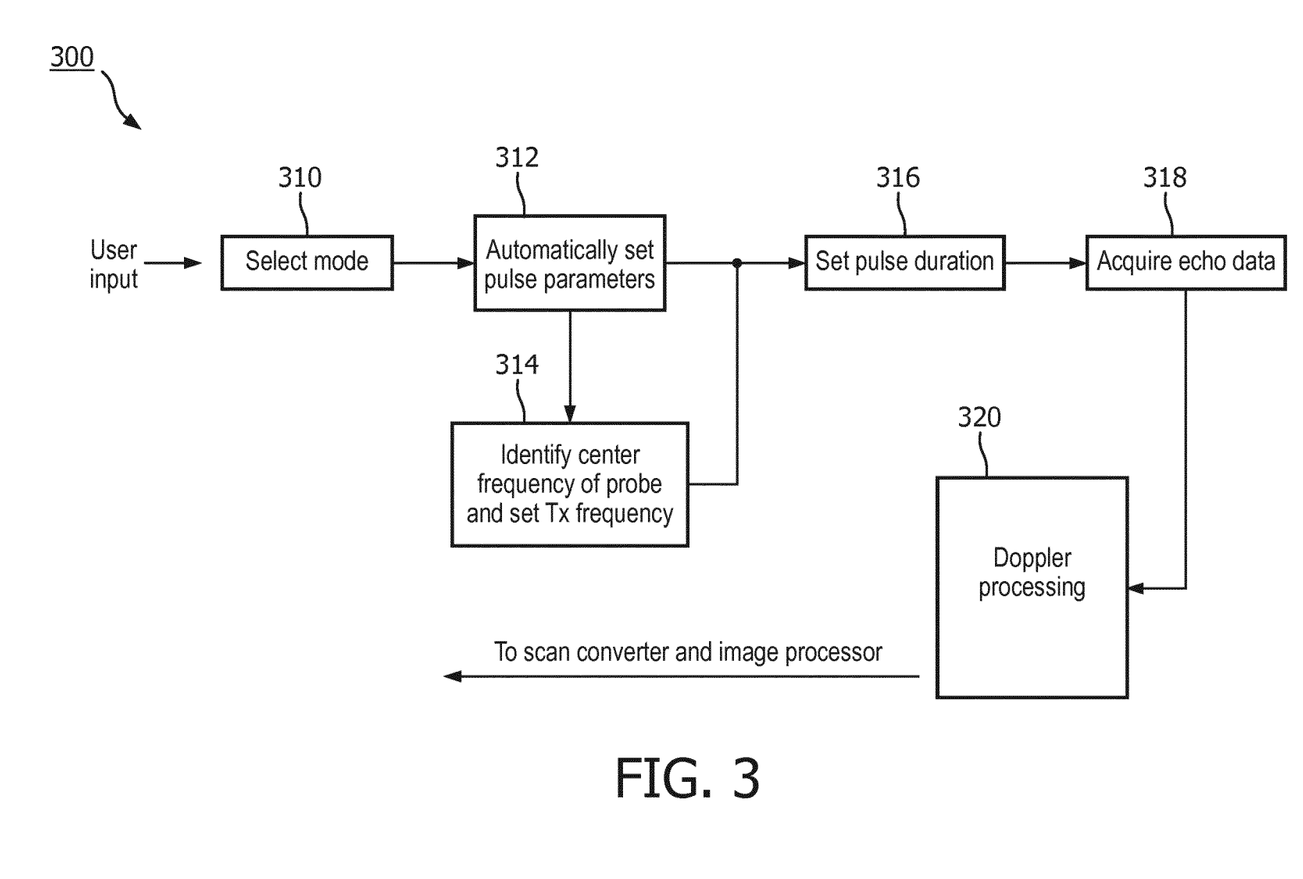
FIG. 3 is a flow diagram of a process for color Doppler imaging in accordance with the present disclosure.

FIG. 3 shows a flow diagram of a process 300 of color Doppler imaging which may be used to ultrasonically detect the presence of renal calculi or another type of calculus in tissue. As shown in block 310, the process may begin by the selection of a color Doppler mode, which may occur responsive to user inputs. The ultrasound imaging system may be configured for ultrasonically scanning and displaying images in any one of a plurality of color Doppler modes, including a first mode (e.g., conventional Colorflow or CPA imaging modes) and a second mode (e.g., a modified Colorflow or CPA mode, also referred to as kidney stone detection mode). The system may apply a different set of pre-stored or automatically selected configuration parameters or settings during each mode. For examples, as previously described, the system may store in memory a plurality of pulse configuration parameters which may include different pulse duration settings for each of the different modes. A first pulse duration setting may be applied when the system is operating in the first mode and a different pulse duration setting may be applied when the system is operating in the second mode. In the first mode, the system may apply a longer pulse setting (e.g., to cause pulses having at least 6 or more cycles to be transmitted while scanning). In the second mode, the system may apply a shorter pulse setting (e.g., to cause pulses having up to 4 cycles to be transmitted while scanning). Thus, as shown in block 312, certain parameters or settings may automatically applied by the system responsive to the selection of a mode. For example, following activation of the kidney stone detection mode, the system may automatically set the transmit frequency to a center frequency of the probe or to a frequency that is close to the center frequency (e.g., within 30% of the center frequency of the probe). In some examples, the kidney stone detection mode may include a user interface which provides the user with the ability to further adjust the transmit frequency, although in some systems, the transmit frequency may be automatically set as described above and not be further adjustable.

In some examples, as shown in block 314, the ultrasound system may automatically identify the center frequency of the probe that is coupled to the system responsive to selection of the second mode. Typically when a probe is connected to an ultrasound system, the system either detects the type of probe or request user input identifying the type of probe. The center frequency may be identified by the system by referencing a lookup table or specifications stored in memory for the types of probes that are configured to operate with that particular ultrasound system. As further shown in block 314, the ultrasound system may automatically set the transmit frequency to the center frequency of the probe. In some examples, the preset values applied by the system may be further configurable by the user. For example, the system may provide a user interface for receiving user inputs to further configure one or more of the pre-set parameters (e.g., the transmit frequency). The process may then continue with acquiring the echo data, as shown in block 318 and processing the echo data, by at least a Doppler processor, as shown in block 320. The color data output by the Doppler processor is then coupled to a scan converter and image processor for generating ultrasound images for display.

Figure 4A:
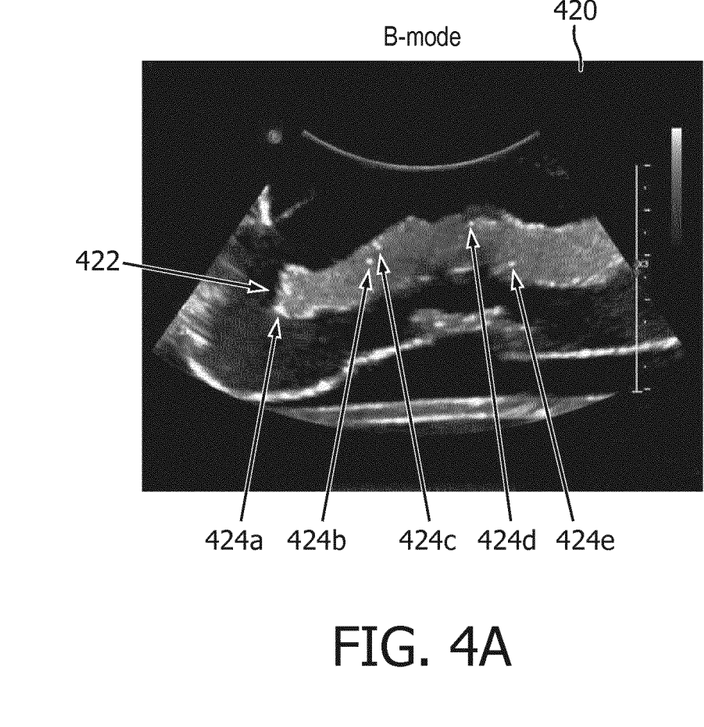
FIGS. 4A-4D are color Doppler images obtained in accordance with the present disclosure.
Figure 4B:
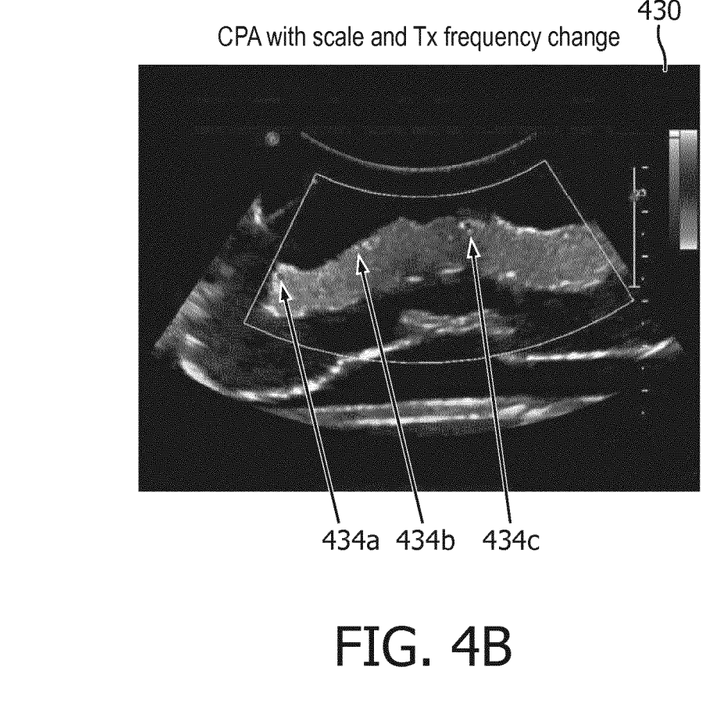

FIGS. 4A-4D show ultrasound images in accordance with some examples herein. FIG. 4A shows a B-mode image 420 of a kidney tissue phantom 422. As can be seen in FIG. 4A, several points in the image (e.g., 424a, 424b, 424c, 424d, and 424e) have relatively higher intensities than the surrounding tissue suggesting the presence of renal calculi. However, it is difficult to determine from the B-mode image alone if the higher intensity points in fact correspond to locations renal calculi. In FIG. 4B, which shows a modified CPA image 430 of the same tissue phantom, the B-mode image data has been overlaid with color data. Unlike a conventional CPA image, the color data associated with moving tissue (e.g., blood flow) is not displayed in image 430. Instead, only color data associated with the twinkling artifact is displayed in the image 430. The image 430 was acquired using the EPIQ ultrasound system and the C5-1 curved array transducer probe manufactured by PHILIPS. Additionally, the transmit frequency was set to 2.5 MHz and the pulse repetition frequency (PRF) was set to 9000 Hz. While the modified CPA image 430 is an improvement over the B-mode grayscale data alone for the purposes of identifying renal calculi, it may still results in some false positive identification. For example, image 430 has now isolated a fewer possible locations (e.g., 434a, 434b, and 434c) from the larger number of bright spots in the image 420 on the left, each of which may be further studies to confirm a diagnosis.

Figure 4C:
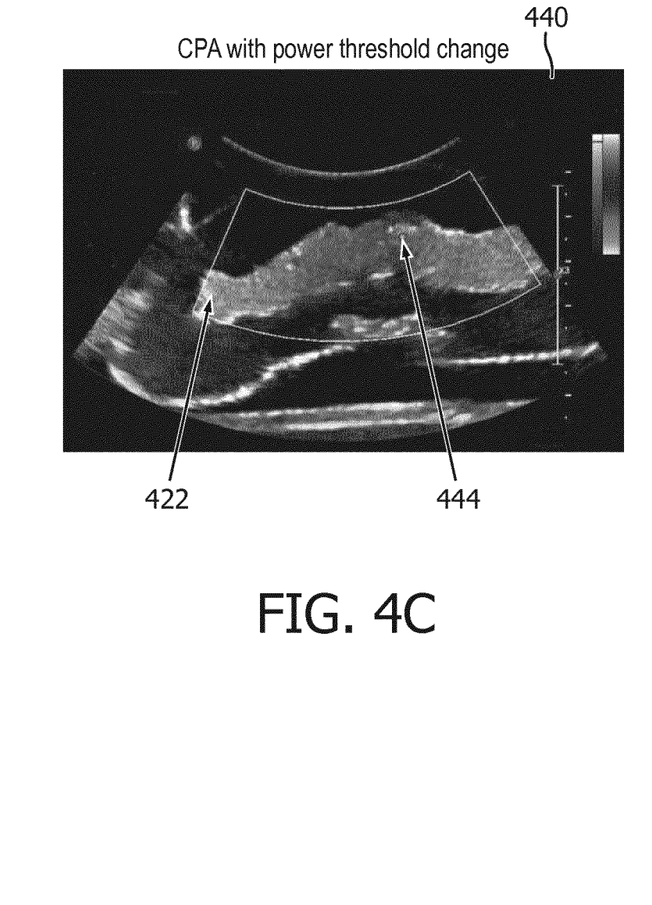
Figure 4D:
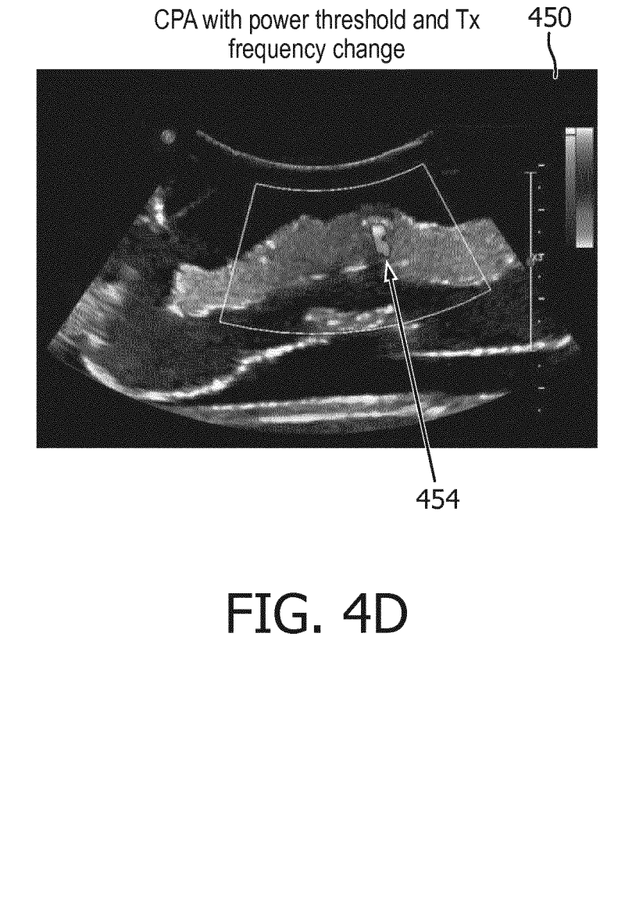

Referring now also to FIGS. 4C and 4D, which shows additional modified CPA images 440 and 450 of the same tissue phantom, the number of possible locations of kidney stones have been further reduced by enhancing the twinkling artifact in accordance with the present disclosure. In these two examples, the images were again acquired using the EPIQ ultrasound system and the C5-1 curved array transducer probe manufactured by PHILIPS, with an increased PRF as compared to the image 430. The PRF for images 440 and 450 was set to 1200 Hz and the tissue was scanned with 3.5 MHz and 2.0 MHz ultrasound waves, respectively. While the twinkling artifact in a color Doppler image is believed to be independent of the transmit frequency, in accordance with the examples herein, the transmit frequency is preferably set to the center frequency or frequency close to the center frequency of the probe, which is typically a lower frequency than may be used for conventional Doppler imaging, in order to increase the power of the beam through the imaged region. In both images 440 and 450, only a single renal calculus is indicated by the presence of a twinkling artifact at a single location. In the image 450 on the right, the twinkling artifact is significantly more visible (e.g., includes a larger number of color pixels) than in the image 440 on the left, which may be due to the increased power applied via the ultrasound pulses to the stone (e.g., as resulting from setting the transmit frequency closer to the center frequency of the probe), which in turn may increase the area and/or intensity of the twinkling artifact.

Figure 5:
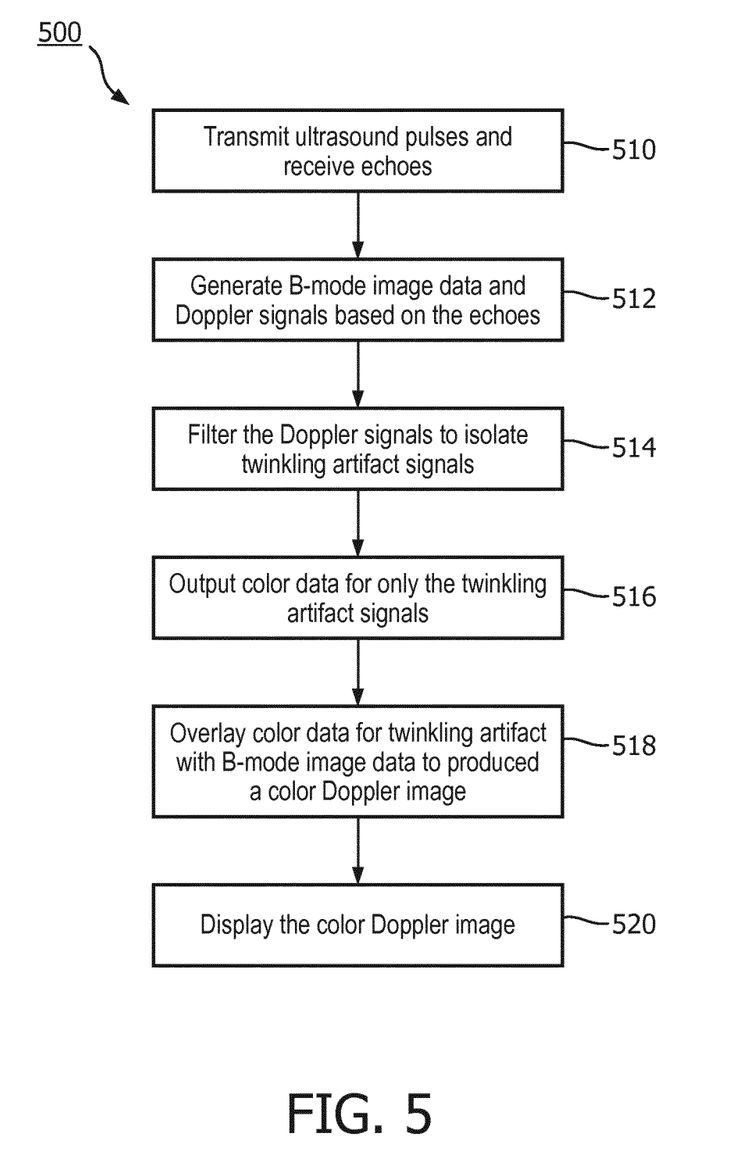
FIG. 5 is flow diagram of a process for color Doppler imaging in accordance with the present disclosure.

FIG. 5 shows a process 500 in accordance with further examples is described. Once a mode has been selected and parameters have been set, the user may acquire the image data by scanning the subject, as shown by the process 500. During the scan, pulsed-wave ultrasound is transmitted to the region of interest and ultrasound echoes are received by the probe. The echoes are coupled to signal processing circuitry and then subsequently to B-mode and Doppler processors (as shown in block 514) for generation of image data. The echoes are used to produce both B-mode image data (i.e., grayscale data) and Doppler image data (i.e., color data). When operating in the relevant mode, in the color Doppler signal path, additional processing occurs to isolate the Twinkling Artifact, which may be indicative of the presence of renal calculi.

If the system is operating in the kidney stone detection sub-mode of the color Doppler imaging mode, the signals are passed through one set of filters, whereas if the system is operating in the conventional modes for color Doppler imaging, the signals are passed through a different set of filters. Specifically, when the former is true, the signals are passed through an intensity filter of the Doppler processor to isolate the Doppler signals associated with the twinkling artifact. If the latter (e.g., conventional modes) apply, the signals are filtered in a manner which retains the lower amplitude signals while rejecting higher amplitude signals. Doppler processing in this step may occur in accordance with any of the examples herein, such as the examples described with reference to FIG. 3.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A method of color Doppler imaging, comprising:
   selecting one of a plurality of color Doppler imaging modes, wherein the plurality of color Doppler imaging modes comprises a colorflow mode and a color power angio mode;
   transmitting with a probe of an ultrasound imaging system, ultrasound pulses towards a region of interest in a subject, the ultrasound pulses comprising a first plurality of ultrasound pulses having a first pulse duration responsive to a selection of the colorflow mode and a second plurality of ultrasound pulses having a second pulse duration shorter than the first pulse duration responsive to a selection of color power angio mode;
   receiving with the probe echoes responsive to the ultrasound pulses;
   generating B-mode image data and Doppler signals based on the ultrasound echoes;
   filtering the Doppler signals with a first filter when the colorflow mode is selected and with a second filter when the color power angio mode is selected, wherein the filtering with the second filter includes rejecting lower intensity signals which have amplitudes below a threshold amplitude and passing higher intensity signals which have amplitudes above the threshold amplitude;
   generating color data based on the higher intensity signals;
   overlaying the color data with the B-mode image data to produce a color Doppler image; and
   displaying the color Doppler image in a kidney stone detection interface.

2. The method of claim 1, wherein the ultrasound pulses comprise ultrasound at a transmit frequency, the method further comprising:
   activating, responsive to user input, one of the plurality of color Doppler imaging modes of the ultrasound imaging system; and
   automatically setting, responsive to said activating, the transmit frequency to a center frequency of the probe or to a frequency within 30% of the center frequency of the probe.

3. The method of claim 2, further comprising automatically identifying the center frequency of the probe responsive to said activating.

4. The method of claim 3, further comprising providing a user interface for adjusting the threshold amplitude, the transmit frequency, a pulse duration, a pulse repetition frequency, selecting one of the plurality of color Doppler imaging modes, or combinations thereof.

5. The method of claim 1, wherein filtering with the first filter comprises filtering the Doppler signals to reject signals above the threshold amplitude.

6. The method of claim 1, wherein the first ultrasound pulses comprise pulses having 6 or greater number of cycles per pulse and wherein the second ultrasound pulses comprise pulses having 5 or fewer number of cycles per pulse.

7. A non-transitory computer-readable medium comprising executable instructions, which when executed cause a processor of medical imaging system to perform any of the methods of claims 1-5, or 6.

8. An ultrasound imaging system configured to perform color Doppler imaging, the system comprising:
- a probe configured to transmit ultrasound pulses to a region of interest in a subject and receive ultrasound echoes responsive to the pulses;
- a user interface configured to receive user input for selecting one of a plurality of color Doppler imaging modes;
- a non-transitory memory which stores a plurality of pulse configuration parameters including a first set of pulse configuration parameters associated with a colorflow imaging mode and a second set of pulse configuration parameters associated with a color power angio imaging mode;
- a transmit controller configured to cause the probe to transmit first pulses in accordance with the first set of pulse configuration parameters responsive to a selection of the colorflow imaging mode and second pulses in accordance with the second set of pulse configuration parameters responsive to a selection of the color power angio imaging mode, wherein the first pulses are longer than the second pulses;
- a signal processor configured to generate echo signals based on ultrasound echoes received by the probe;
- a B-mode processor configured to generate B-mode image data based on the echo signals;
- a Doppler processor configured to generate Doppler signals based on the echo signals, wherein the Doppler processor is further configured, responsive to the selection of the colorflow imaging mode to apply a first filter to the Doppler signals and responsive to the selection of the color power angio imaging mode, to apply a second filter to the color Doppler signals to filter out the Doppler signals below a threshold amplitude, retain the Doppler signals above the threshold amplitude, and generate color data for only the retained Doppler signals; and
- a display configured to display an overlay of the B-mode image data and the color data.

9. The system of claim 8, wherein the first filter is configured to filter out Doppler signals above the threshold amplitude.

10. The system of claim 8, wherein the Doppler processor includes an amplitude threshold filter configured to filter out the Doppler signals below the threshold amplitude and a wall filter configured to filter out signals below a predetermined frequency.

11. The system of claim 8, wherein the threshold amplitude corresponds to an echo intensity of at least 40 dB above an echo intensity associated with a fluid or soft tissue.

12. The system of claim 8, wherein the non-transitory memory further stores executable instructions for automatically identifying, responsive to the selection of the color power angio imaging mode, the center frequency of the probe coupled to the system and setting the transmit frequency for the second pulses to the center frequency of the probe or to a frequency within 30% of the center frequency of the probe.

13. The system of claim 8, wherein the user interface is further configured to receive user input for adjusting the transmit frequency.

14. The system of claim 8, wherein the second pulses comprise pulses having 4 or fewer cycles per pulse.

15. The method of claim 1, wherein a frame rate of the color power angio imaging mode is greater than a frame rate of the first imaging mode.

16. The method of claim 1, wherein the threshold amplitude comprises 40 dB above an amplitude of a blood flow or a tissue.

17. The system of claim 8, wherein the threshold amplitude comprises 35 dB above an amplitude of a blood flow or a tissue.

* * * * *